(12) United States Patent
Voix et al.

(10) Patent No.: US 8,903,114 B2
(45) Date of Patent: Dec. 2, 2014

(54) IN-EAR DEVICE WITH SELECTABLE FREQUENCY RESPONSE

(75) Inventors: Jérémie Voix, Montreal (CA); Jean-Nicolas Laperle, Montreal (CA)

(73) Assignee: Sonomax Technologies Inc., Montréal, QC (CA)

( * ) Notice: Subject to any disclaimer, the term of this patent is extended or adjusted under 35 U.S.C. 154(b) by 315 days.

(21) Appl. No.: 12/929,052

(22) Filed: Dec. 27, 2010

(65) Prior Publication Data

US 2011/0158421 A1    Jun. 30, 2011

Related U.S. Application Data

(60) Provisional application No. 61/282,176, filed on Dec. 24, 2009.

(51) Int. Cl.
*H04R 25/00*    (2006.01)
*A61F 11/08*    (2006.01)
*A61F 11/06*    (2006.01)
*A61B 7/02*    (2006.01)

(52) U.S. Cl.
CPC ........... *A61F 11/08* (2013.01); *A61F 2011/085* (2013.01)
USPC ............................... 381/329; 381/72; 181/135

(58) Field of Classification Search
CPC .. H04R 1/1016; H04R 1/1083; H04R 1/1091; H04R 2460/11; H04R 2460/15; H04R 2460/17; H04R 25/652; H04R 25/48
USPC .................... 381/72, 322, 325, 329; 128/864; 181/126, 135

See application file for complete search history.

(56) References Cited

U.S. PATENT DOCUMENTS

| | | | |
|---|---|---|---|
| 3,637,040 A | 1/1972 | Gorman | |
| 5,832,094 A | 11/1998 | Le Her et al. | |
| 6,082,485 A * | 7/2000 | Smith | 181/135 |
| 6,286,622 B1 * | 9/2001 | Tiemann | 181/135 |
| 6,339,648 B1 | 1/2002 | McIntosh et al. | |
| 6,687,377 B2 | 2/2004 | Voix et al. | |
| 6,688,421 B2 * | 2/2004 | Dyer et al. | 181/130 |
| 6,754,357 B2 | 6/2004 | McIntosh et al. | |
| 7,182,087 B1 * | 2/2007 | Marsh | 128/867 |
| 7,478,702 B2 * | 1/2009 | Berg et al. | 181/135 |
| 7,688,983 B2 | 3/2010 | Voix et al. | |

* cited by examiner

*Primary Examiner* — Vivian Chin
*Assistant Examiner* — Ammar Hamid
(74) *Attorney, Agent, or Firm* — Equinox IP; Franz Bonsang

(57) ABSTRACT

An in-ear device comprises a main body for placement in the outer ear of a wearer and has at least two derivative canals each containing a filtering medium differing from one another in terms of their frequency suppression capabilities, and a preferably rotatable knob enabling selection of the respective filtering canal without the need for removal of the device from the ear.

19 Claims, 4 Drawing Sheets

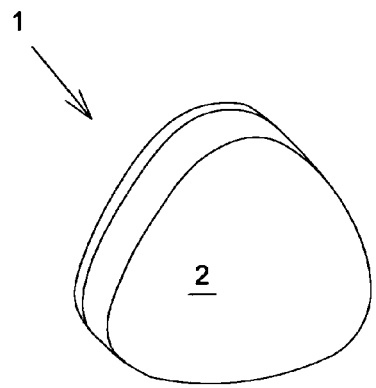
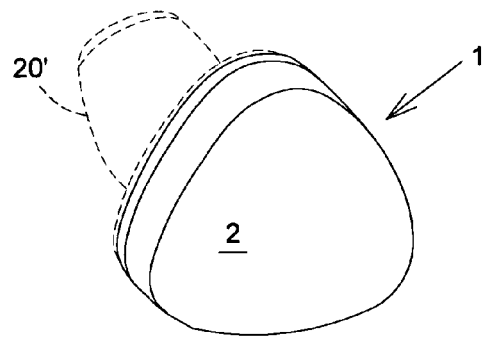
FIG.1      FIG.2
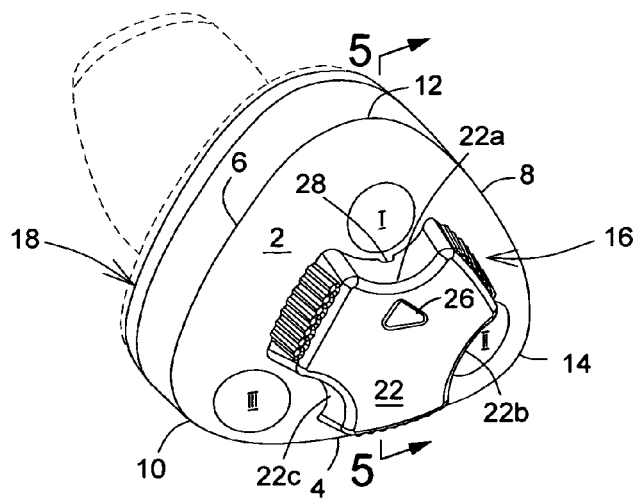
FIG.3

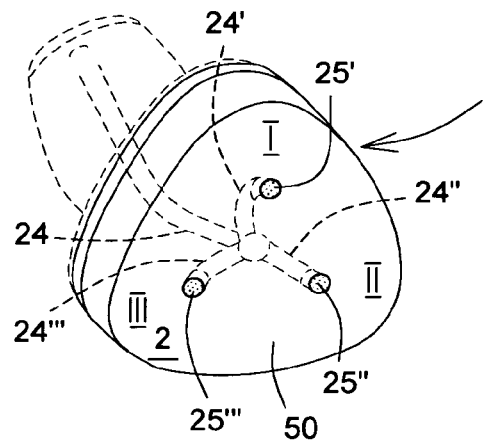 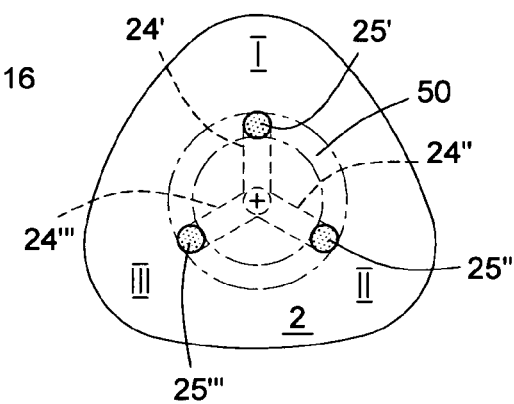
FIG.4a  FIG.4b
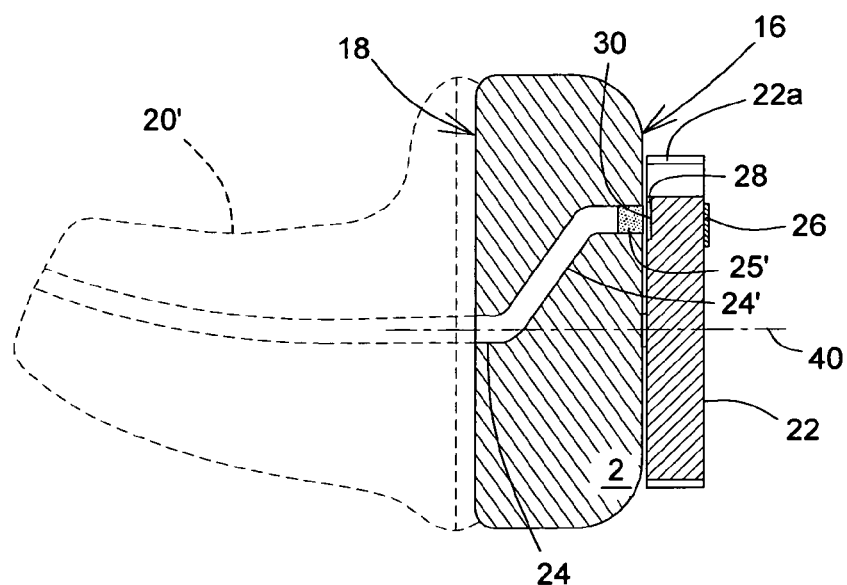
FIG.5

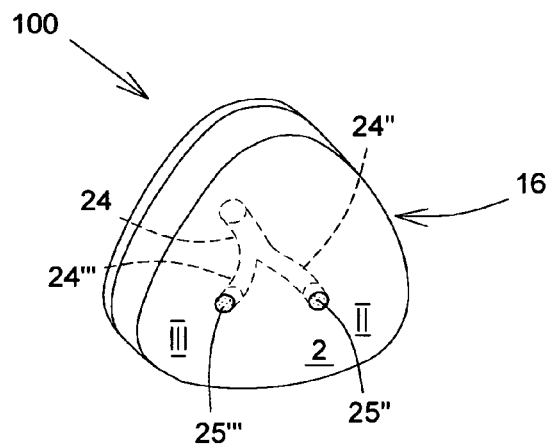
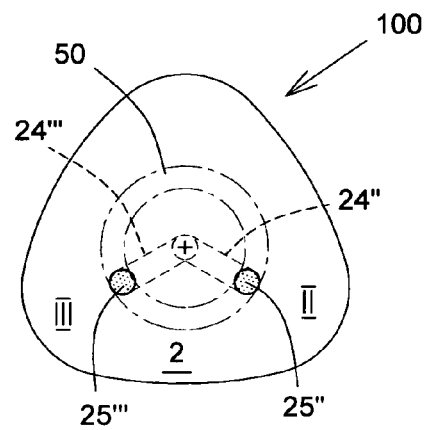
FIG.6a  FIG.6b
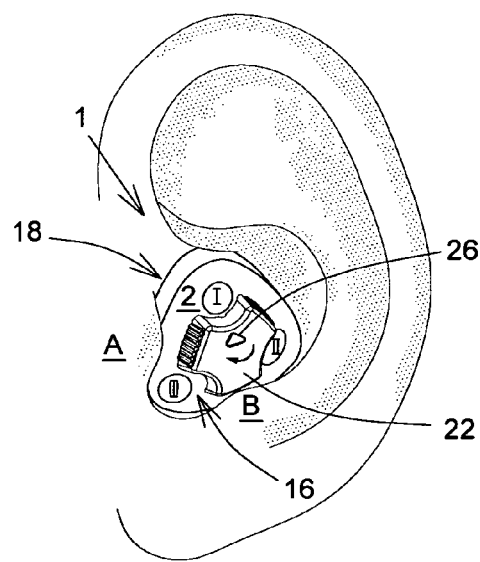
FIG.7

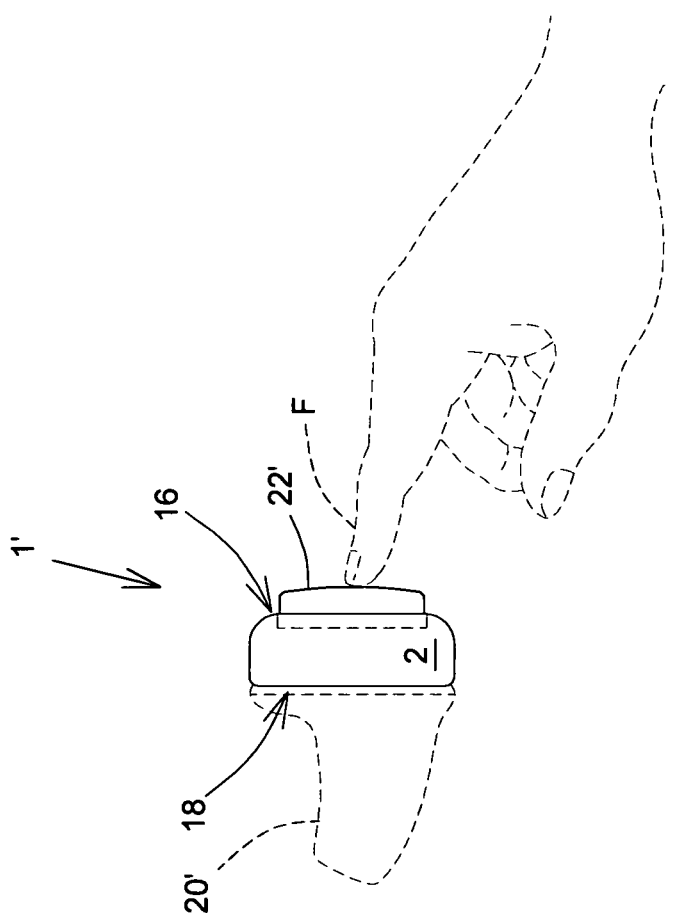

IN-EAR DEVICE WITH SELECTABLE FREQUENCY RESPONSE

CROSS REFERENCE TO RELATED APPLICATIONS

Benefit of U.S. Provisional Application for Patent Ser. No. 61/282,176 filed on Dec. 24, 2009, which is incorporated herein by reference, is hereby claimed.

FIELD OF THE INVENTION

This invention relates to in-ear devices, such as intra-aural hearing protectors (earplugs), earphones, or hearing-aide devices, and more specifically to an in-ear device which has a selectable frequency response with pre-determined values, the selection being made with the device being properly positioned inside the wearer's ear.

BACKGROUND OF THE INVENTION

High-level sounds, and particularly the recurrence thereof, are known to cause hearing impairment, and in extreme cases, the loss of hearing. In order to avoid the hearing impairments, numerous types of hearing protectors for noise reduction has been proposed to be used in different fields and uses such as military, industrial applications and music.

One of the most common hearing protectors is a foam earplug. Foam earplugs are rolled-down and inserted into the ear canal. When the rolling pressure is interrupted, the plug expands to fit the inner morphology of the ear. One of the limitations of foam earplugs is that they are intended to filter a broad range of sound frequencies. If the wearer needs protection for a specific range of sound frequencies—or when the user needs a less attenuating product in order to hear voice or warning signals—he will have to completely remove the earplugs and take a new pair of plugs made of different material, or filter with passive or active acoustical means. This procedure represents a disadvantage, since it renders the user unprotected during the transition.

There is in the market an ear protective device that can be adjusted according to two different frequency response operating modes. This device has the possibility to switch between two different levels of sound attenuation. However, the device requires that it be removed from the ear before changing from one operating mode to the other because of the rotating knob that rotates within a plane substantially parallel to the axis of the entrance of the ear canal (or about an axis substantially perpendicular to a plane of the outer ear). Again, this procedure renders the user unprotected during the transition.

Accordingly, there is a need for an improved in-ear device that enables the wearer to switch between different levels of attenuation protection, without compromising his auditory protection.

BRIEF SUMMARY OF THE INVENTION

In order to overcome the limitations and problems discussed above, the main objective of the present invention is to provide for an improved in-ear device that enables the wearer to switch between different levels of sound protection, without compromising his auditory protection.

An advantage of the present invention is to provide an in-ear device that can be selectively adjusted for filtering a specific range or level of sound frequencies.

A further advantage of the present invention is to provide an in-ear device that will allow the wearer to select the degree of attenuation or frequency range protection according to the acoustic conditions of the environment, via a rotating button, a push toggle button or the like, or even a combination thereof.

Another advantage of the invention is to provide an in-ear device that can easily be adjusted without removing the same from the wearer's ear.

Yet another advantage of the invention is to provide an in-ear device that can be adjusted in such a way that it helps to keep the device in the wearer's ear, by applying positive pressure thereon, and optionally with a rotational motion towards natural insertion of the device inside the wearer's ear, especially when the protrusion is pre-shaped to fit the ear canal.

According to an aspect of the present invention, there is provided an in-ear device for selectively adjusting the range or level of sound frequencies reaching the inner ear of a wearer's ear, therefore having a selectable frequency response, said device comprising a main body having an innermost face and an outermost face, a canal inside the main body and extending from an inner end of the innermost face to an outer end of the outermost face of the main body and splitting into at least two derivative canals adjacent the outermost face within a generally annular zone defined thereon, each said canals being at least partially filled with a respective filling material, a knob, preferably rotatably attached to the outermost face of the main body and defining a peripheral edge thereof extending beyond the inner zone so as to cover the inner zone, said knob having a channel formed within an inner surface thereof, said channel extending generally radially from the knob periphery to an inner end thereof adjacent the annular zone whereby the channel being selectively in fluid communication with a respective said derivative canal upon rotation thereof.

Conveniently, the knob rotates about a knob axis generally coaxial with an axis of the annular zone.

Additionally, the knob is mounted in the main body in such a way that it can be easily rotated from one of the positions to the other without compromising the filtering capabilities of the device. In general, the device of the invention has three different positions, each position representing a filtering mode for a specific range or level of sound frequencies, or type of sound. The knob can be easily rotated from one position to the other, without the need to remove the device from the ear. Additionally, the knob of the invention comprises means that will indicate to the wearer the appropriate position of the knob in one of the positions.

Typically, the main body has at least three sides, a first side of said at least three sides being shaped to fit the tragus of a wearer's ear, and a second side of said at least three sides being shaped to fit an antitragus of a wearer's ear.

In one embodiment, the knob is a push toggle button movably mounted on the outermost face of the main body.

These and other advantages and objects will be apparent in view of the following detailed description in connection with the accompanying drawings.

BRIEF DESCRIPTION OF THE DRAWINGS

Further aspects and advantages of the present invention will become better understood with reference to the description in association with the following figures, in which similar references used in different figures denote similar components, wherein:

FIG. 1 is a perspective view of one embodiment for the main body according to the present invention;

FIG. 2 is a perspective view of another embodiment for the main body according to the present invention;

FIG. 3 is a perspective view of a device in accordance with one of the embodiments of the present invention;

FIG. 4a is a perspective view of the embodiment of FIG. 3 where the knob has been omitted to facilitate visualising the elements inside the main body;

FIG. 4b is a front view of the embodiment of FIG. 4a;

FIG. 5 is a side sectional view on the line 5-5 in FIG. 3 depicting the surroundings of the knob when operating on filtering mode I;

FIG. 6a is a perspective view of an embodiment wherein the main body has only two derivative canals;

FIG. 6b is a front view of the embodiment of FIG. 6a;

FIG. 7 is a front view of the device of FIG. 1 in the final position inside the left-hand-side ear of a wearer; and FIG. 8 is a side view similar to FIG. 5 of another embodiment for the main body according to the present invention, showing a push toggle button.

DETAILED DESCRIPTION OF THE PREFERRED EMBODIMENTS

In FIGS. 1 and 2 there is depicted the device 1 of the invention comprising a main body 2. In general, the main body 2 can be designed and shaped so as to be safely placed in the outer ear of a specific wearer's ear. In FIGS. 1 and 2 are depicted two possible embodiments for the main body 2 according to the present invention. FIG. 1 represents the more general shape of main body 2; FIG. 2 represents an embodiment including a protrusion 20' intended to be inserted inside of a wearer's ear canal.

Referring to FIG. 3, there is shown a specific embodiment of the invention comprising a main body 2 having three sides 4, 6 and 8. The sides of the main body 2 are generally equal to one another, forming a main body 2 quasi-triangular in shape. By way of example, and not a limitation, the three sides 4, 6 and 8 of the main body 2 are convex; however, they might be shaped to resemble other geometrical forms. The device 1 might have at least three sides provided that at least two of the sides are designed and shaped in a way that a first side 6 fits the tragus A of a wearer's ear, and the second side 4 fits the antitragus B of a wearer's ear (see FIG. 7). The main body 2 also includes at least three tips. As shown in FIG. 3, two adjacent sides are united by one of the tips 10, 12 or 14. Tips 10, 12 and 14 might have any geometrical form; preferably tips 10, 12 and 14 are rounded. As viewed in FIG. 3 the main body 2 includes an outermost face 16 and an innermost face 18. The outermost face 16 might include markings representing the applicable filtering modes on the device 1. The main body 2 might have at least two filtering modes; as reference, in FIG. 3 the device 1 includes the filtering modes I, II and III.

Referring to FIG. 4a, it shows the canal 24 inside the main body 2. The canal 24 extends from an inner end of the innermost face 18 to an outer end of the outermost face 16. Before reaching the outer end of the outermost face 16, the canal 24 splits into at least two derivative canals adjacent to the outermost face within a generally annular zone 50 defined thereon. In general, the number of derivative canals depends on the number of filtering modes applicable on the device 1; in FIGS. 4a and 4b there is shown a device 1 including three filtering modes I, II and, III and, consequently, three derivative canals 24', 24" and 24''' associated to the filtering modes I, II and III, respectively. The interior of each derivative canals 24', 24" and 24''' is at least partially filled with a respective filtering material 25', 25" and 25''' specially manufactured to filter a specific range or level of sound frequencies, such as a foam plug of a predetermined density for a corresponding desired frequency response; the material composition is such as to let through only a specific range or level of sound frequencies. The derivative canals 24', 24" and 24'''might be entirely filled with the filtering materials; more preferably the derivative canals 24', 24" and 24''' are partially filled. In general, each derivative canal 24', 24" and 24''' is filled with a different material. The filtering capability associated to the modes I, II and III depends on the respective filling material 25', 25" and 25'''. By way of example, and not a limitation, the filling material 25', 25" and 25''' can be selected as to filter all the frequencies, but the frequencies of the human voice, or to filter the frequencies associated with impulse noises. The filling material 25', 25" and 25''' can be selected from various materials such as, but not limited to, solids or porous solids (metal or plastic foams), layers of plastic or metallic meshes (Knowles electronics dampers), and properly designed filters (as custom ISL filters designed by Institut Saint-Louis from France—expansion chamber or the like), and any combination thereof. The extreme positioning of the derivative canals 24', 24" and 24''' on the outermost face 16 is so that they are equidistant to the center of the generally annular zone 50. The annular zone 50 defines an inner zone for the rotation of the knob 22 as explained below.

The device 1 also comprises a knob 22. In FIG. 3, the knob 22 is shown on the outermost face 16 of the main body 2. The knob 22 is rotatably attached to the outermost face of the main body 2 so as to easily allow a wearer to turn the knob 22 towards the desired filtering mode I, II or III. The direction of rotation of the knob 22 depends on the ear in which the device 1 is intended to be used. If the device 1 is inside the wearer's right ear, the rotation will be allowed in counterclockwise direction; conversely, if the device 1 is inside the wearer's left ear, the rotation will be allowed in clockwise direction. By limiting the rotational movement as just disclosed, the knob 22 helps to keep the device 1 in proper position inside a wearer's ear by applying positive pressure thereon, towards natural insertion of the device inside the wearer's ear, especially when the protrusion 20' is pre-shaped to fit the ear canal. In order to switch from filtering position I towards filtering mode II, and from filtering mode II towards filtering mode III, the knob 22 could have an indexing system (not shown) based on a releasable spring, or another releasable friction device (not shown). When the wearer wants to change the filtering mode, he just has to exert some pressure on the knob 22 against the body 2 and the inward movement of the knob 22 leads it to the released position; the wearer is able to rotate the knob 22 to the desired filtering mode as described above. Once the knob is in the proper position, the user stops exerting pressure on the knob 22, to allow it to return to the operational position. The knob 22 rotates about a knob axis 40 generally coaxial with an axis of the annular zone 50 (or rotates within a plane substantially perpendicular to the axis of the entrance of the ear canal, or about an axis substantially parallel to a plane of the outer ear). The knob 22 defines a peripheral edge extending beyond the outer zone of the annular zone 50 so as to cover the outer zone. By way of example, and not of limitation, the knob 22 of FIG. 3 includes three recesses 22a, 22b and 22c; however, the recesses 22a, 22b and 22c might be replaced by a protrusion or any other geometrical form without affecting the functionality of the device 1. The device 1 might have at least two recesses. Each recess faces a corresponding one of the filtering modes when the device 1 is filtering the sound according to the wearer's needs. The recess 22a might include a marking 26 intended to indicate on what filtering mode the device 1 is operating. In FIG. 3 the marking 26 is shaped to resemble an arrow's tip indicating the device 1 is filtering sound according to the properties of the filtering material 25' inside canal 24'. More preferably, the marking 26 is a protrusion that will allow the wearer to determine, just by sensing with the tip of his fingers, on what filtering mode the device 1 is operating. The thickness of the surroundings of the recesses 22a—the one indicating the operating filtering mode—is always smaller than the rest of the body of the knob 22, thus defining an open end 28. In FIG. 5 the knob 22 is depicted in the filtering mode I, and the open end 28 at the knob periphery is formed due to the differences in thickness in the surroundings of the recess 22a. In order to let the sound enter inside the open end 28 and, consequently, inside the inner ear of the wearer, there is a channel 30 between the knob 22 and the outermost face 16 of the main body 2. The channel 30 is formed within an inner surface of the knob 22, and extends generally radially from the knob periphery at the open end 28 thereof to an inner end thereof adjacent to the annular zone 50 whereby the channel 30 is selectively in fluid communication with a respective said derivative canal upon rotation of the knob 22. The thickness or depth of the channel 30 is from about 0.5 mm to about 2 mm while the width of the channel is typically about twice the thickness. The channel 30 is in direct communication with one of the derivative canals 24', 24" and 24''', and their respective filtering materials 25', 25", 25''', depending on the filtering mode I, II and III selected by the wearer. In FIG. 5, the channel 30 is in fluid communication with derivative canal 24'. As the sound travels from the open end 28 to the inner ear of the wearer—first through the corresponding derivative canal 24' and then through the canal 24—it passes through the filtering material 25' wherein only a specific range or level of sound frequencies is allowed to continue. The device 1 might include appropriate means to indicate the wearer that he has reached the desired position—filtering mode. The device 1 might have an indentation associated to each recess 22a, and three correspondent counterparts in the main body 2, in the surrounding of the marks indicating the filtering modes I, II or III. When the recess 22a is about to reach the desired position, the indentation and its counterpart will make a sound indicating the proximity of the right position.

Referring to FIGS. 6a and 6b, there is an additional embodiment of the invention depicting the device 100 wherein one of the filtering positions is designed to substantially block all sound frequencies. The result will be a device 100 with a filtering position substantially hindering the entrance of sound into the inner ear of the wearer according to the inherent attenuation characteristics of the in-ear device 100. In this embodiment, the device 100 only has two derivative canals, 24" and 24'''. The derivative canals 24' is omitted and its corresponding space is occupied by the material of the main body 2, creating a barrier to the entrance of the sound from open end 28 with the knob 22 in the corresponding position.

Referring now to FIG. 8, there is shown another embodiment 1' in accordance with the present invention, in which the knob 22' is a push toggle button movably mounted on the outermost face 16 of the main body 2, to switch between the available filtering modes, under the positive pressure applied by an external force as represented by a wearer's finger F in stippled lines.

Although the present invention has been described with a certain degree of particularity, it is to be understood that the disclosure has been made by way of example only and that the present invention is not limited to the features of the embodiments described and illustrated herein, but includes all variations and modifications within the scope and spirit of the invention as hereinafter claimed.

We claim:

1. An in-ear device for selectively adjusting the range or level of sound frequencies reaching the inner ear of a wearers ear, said device comprising a main body having an innermost face and an outermost face, a canal inside the main body and extending from an inner end of the innermost face to an outer end of the outermost face of the main body and splitting into at least two derivative canals adjacent the outermost face within a generally annular zone defined thereon, each said canals being at least partially filled with a respective filtering material, a knob movably attached to the outermost face of the main body and defining a peripheral edge thereof extending beyond the inner zone so as to cover the inner zone, said knob having a channel formed within an inner surface thereof, said channel extending generally radially from an open end thereof at the knob periphery to an inner end thereof adjacent the annular zone, the inner end of the channel being selectively in fluid communication and in alignment with the outer end of only one of said at least two derivative canals at a time upon rotation thereof relative to the main body so as to selectively allow external sound to flow therethrough and reach the inner ear of the wearer's ear.

2. An in-ear device according to claim 1 wherein the knob is rotatably attached to the outermost face for rotation about a knob axis generally coaxial with an axis of the annular zone.

3. An in-ear device according to claim 2 wherein the knob is rotatable about a knob axis generally coaxial with an axis of the annular zone.

4. An in-ear device according to claim 3 wherein the knob is rotatable about said axis between filtering positions corresponding to the derivative canals.

5. An in-ear device according to claim 4 wherein the knob is mounted in the main body in such a way that in use it is adapted for rotation from one of said positions to another without compromising the filtering capabilities of the device.

6. An in-ear device according to claim 5 wherein the device has at least two different filtering positions, each position representing a filtering mode for a specific range or level of sound frequencies or type of sound.

7. An in-ear device according to claim 6 wherein the device has three filtering positions.

8. An in-ear device according to claim 4 wherein the knob is adapted for rotation from one filtering position to the other, without the need in use to remove the device from the ear.

9. An in-ear device according to claim 4 wherein the knob is indexable into the filtering positions corresponding to the derivative canals.

10. An In-ear device according to claim 4 wherein the knob comprises means that indicate to the wearer the appropriate position of the knob in one of the filtering positions.

11. An in-ear device according to claim 4 wherein the rotational direction of the knob relative to the main body for the purpose of changing the filtering position is predetermined by the ear in which the device is adapted to be placed.

12. An in-ear device according to claim 11 wherein said predetermined direction of rotation is adapted to assist in ensuring continuing effective disposition of the device in the relevant ear of the wearer.

13. An in-ear device according to claim 1 wherein the main body has at least three sides, a first side of said at least three sides being shaped for fitting the tragus of a wearer's ear and a second side of said at least three sides being shaped for fitting an antitragus of a wearer's ear.

14. An in-ear device according to claim 13 wherein means are provided on the main body to indicate the position of the derivative canals.

15. An an-ear device according to claim 2 wherein the main body is so adapted as to provide a blanked-off derivative canal whereby upon selection by rotation of the knob in use the transmission of substantially all sound frequencies to the wearer's ear is hindered by inherent attenuation characteristics of the in-ear device.

16. An in-ear device according to claim 2 wherein the main body is provided with a protrusion adapted for insertion into the ear canal of a wearer.

17. An in-ear device according to claim 16 wherein the protrusion is pre-shaped for fitting insertion into the ear canal of a wearer.

18. An in-ear device according to claim 1 wherein the knob is a push toggle button movably mounted on the outermost face of the main body.

19. An in-ear device according to claim 11 wherein said predetermined direction of rotation is clockwise when the device is adapted to be placed into a wearer's left ear or counterclockwise when the device is adapted to be placed into a wearer's right ear.

\* \* \* \* \*